United States Patent
Reinoso Garcia et al.

(10) Patent No.: US 9,802,884 B2
(45) Date of Patent: Oct. 31, 2017

(54) MIXTURES OF MGDA ENANTIOMERS, AND PROCESS FOR MAKING SUCH MIXTURES

(71) Applicant: BASF SE, Ludwigshafen (DE)

(72) Inventors: Marta Reinoso Garcia, Dossenheim (DE); Markus Hartmann, Neustadt (DE); Kati Schmidt, Ludwigshafen (DE); Matthias Rauls, Blieskastel (DE); Thomas Schmidt, Neustadt (DE); Paul Klingelhoefer, Mannheim (DE); Alfred Oftring, Bad Duerkheim (DE); Somnath Shivaji Kadam, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 46 days.

(21) Appl. No.: 15/021,398

(22) PCT Filed: Sep. 5, 2014

(86) PCT No.: PCT/EP2014/068910
§ 371 (c)(1),
(2) Date: Mar. 11, 2016

(87) PCT Pub. No.: WO2015/036324
PCT Pub. Date: Mar. 19, 2015

(65) Prior Publication Data
US 2016/0221931 A1   Aug. 4, 2016

(30) Foreign Application Priority Data

Sep. 13, 2013 (EP) .................... 13184347
Jun. 23, 2014 (EP) .................... 14173388
Jun. 23, 2014 (EP) .................... 14173393
Jul. 4, 2014 (EP) .................... 14175796

(51) Int. Cl.
*C11D 3/33* (2006.01)
*C07C 227/42* (2006.01)
*C07C 229/24* (2006.01)
*C07C 227/18* (2006.01)
*C07C 227/36* (2006.01)
*C07C 229/16* (2006.01)
*C07C 253/00* (2006.01)

(52) U.S. Cl.
CPC .......... *C07C 229/24* (2013.01); *C07C 227/18* (2013.01); *C07C 227/36* (2013.01); *C07C 229/16* (2013.01); *C07C 253/00* (2013.01); *C11D 3/33* (2013.01)

(58) Field of Classification Search
CPC ..... C11D 3/0094; C11D 3/33; C11D 11/0017; C11D 7/3245; C07C 227/42; C07C 229/24
See application file for complete search history.

(56) References Cited

U.S. PATENT DOCUMENTS 7,671,234 B2    3/2010 Oftring et al.
2012/0248370 A1* 10/2012 Oftring ................. C07C 227/26
                                                      252/182.12
2012/0283473 A1* 11/2012 Oftring ................. C07C 227/42
                                                      562/571

FOREIGN PATENT DOCUMENTS

| DE | 198 19 187 A1 | 11/1999 |
|---|---|---|
| EP | 0 851 023 A2 | 7/1998 |
| WO | WO 2012/150155 A1 | 11/2012 |
| WO | WO 2013/056965 | 4/2013 |

OTHER PUBLICATIONS

International Search Report issued Oct. 24, 2014 in PCT/EP2014/068910.
Written Opinion issued Oct. 24, 2014 in PCT/EP2014/068910.
International Preliminary Report on Patentability issued Jul. 22, 2015 in PCT/EP2014/068910.
Norio Koine, et al., "Preparation and Circular Dichroism of trans(N) and cis(N) Isomers of (L- or D-Alaninate-N,N-diacetato) (aminoacidato)-cobaltate(III) Complexes" Bulletin of the Chemical Society of Japan, vol. 43, No. 6, Jun. 1970, pp. 1737-1743.

* cited by examiner

*Primary Examiner* — Charles Boyer
(74) *Attorney, Agent, or Firm* — Oblon, McClelland, Maier & Neustadt, L.L.P.

(57) ABSTRACT

Mixture of L- and D-enantiomers of methyl glycine diacetic acid (MGDA) or its respective mono-, di or trialkali metal or mono-, di- or triammonium salts, said mixture containing predominantly the respective L-isomer with an enantiomeric excess (ee) in the range of from 10 to 75%.

15 Claims, No Drawings

MIXTURES OF MGDA ENANTIOMERS, AND PROCESS FOR MAKING SUCH MIXTURES

The present invention is directed towards a mixture of L- and D-enantiomers of methyl glycine diacetic acid (MGDA) or its respective mono-, di or trialkali metal or mono-, di- or triammonium salts, said mixture containing predominantly the respective L-isomer with an enantiomeric excess (ee) in the range of from 10 to 75%.

Chelating agents such as methyl glycine diacetic acid (MGDA) and their respective alkali metal salts are useful sequestrants for alkaline earth metal ions such as $Ca^{2+}$ and $Mg^{2+}$. For that reason, they are recommended and used for various purposes such as laundry detergents and for automatic dishwashing (ADW) formulations, in particular for so-called phosphate-free laundry detergents and phosphate-free ADW formulations. For shipping such chelating agents, in most cases either solids such as granules are being applied or aqueous solutions.

Granules and powders are useful because the amount of water shipped can be neglected but for most mixing and formulation processes an extra dissolution step is required.

Many industrial users wish to obtain chelating agents in aqueous solutions that are as highly concentrated as possible. The lower the concentration of the requested chelating agent the more water is being shipped. Said water adds to the costs of transportation, and it has to be removed later when MGDA is to be incorporated in a solid product. Although about 40% by weight solutions of racemic MGDA trisodium salt can be made and stored at room temperature, local or temporarily colder solutions may lead to precipitation of MGDA, as well as nucleating by impurities. Said precipitations may lead to incrustations in pipes and containers, and/or to impurities or inhomogeneity during formulation.

It can be tried to increase the solubility of chelating agents by adding a solubilizing agent, for example a solubility enhancing polymer or a surfactant. However, many users wish to be flexible with their own detergent formulation, and they wish to avoid polymeric or surface-active additives in the chelating agent.

Additives that may enhance the solubility of the respective chelating agents may be considered but such additives should not negatively affect the properties of the respective chelating agent. However, many additives have a negative effect, or they limit the flexibility for later formulations.

It has been additionally found that some samples of MGDA contain a lot of impurities that may limit their applicability in fields such as laundry detergents and ADW. Such impurities are sometimes attributed to disadvantageous colouring especially at a pH value below 10 and olfactory behaviour that sometimes goes with MGDA and other chelating agents, see, e.g., the comparative examples of U.S. Pat. No. 7,671,234.

U.S. Pat. No. 7,671,234 discloses an improved saponification of MGDN,

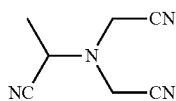

Although U.S. Pat. No. 7,671,234 shows improvements, still more improved colouring and olfactory behaviour is desired.

WO 2012/150155 discloses the improved solubility of pure L-MGDA, compared to racemic MGDA. However, it is tedious to make MGDA and to carefully avoid any racemization. Although it is well possible to synthesize racemic MGDA and to separate off the D-isomer, such a method would result in disposing 50% of the yield or more.

It has further been found that racemic MGDA shows some intolerance against strong bases such as sodium hydroxide. This limits its usefulness in certain applications such as industrial and institutional cleaners that in many instances contain significant amounts of strong bases such as potassium hydroxide or sodium hydroxide.

It was therefore the objective of the present invention to provide highly concentrated aqueous solutions of chelating agents such as MGDA that are stable at temperatures in the range from zero to 50° C., without the addition of surfactants or organic polymers or salts of organic acids. It was further an objective of the present invention to provide chelating agents that show an improved tolerance towards strong bases such as solid potassium hydroxide or solid sodium hydroxide. It was further an objective of the present invention to provide a method for manufacture of highly concentrated aqueous solutions of chelating agents such as MGDA that are stable at temperatures in the range from zero to 50° C. Neither such method nor such aqueous solution should require the use of additives that negatively affect the properties of the respective chelating agent. In particular, neither organic polymers nor salts of organic acids should be necessary to stabilize such solutions.

Accordingly, the mixtures of enantiomers defined at the outset have been found that can be converted into the aqueous solutions that solve the above problems. The mixtures of enantiomers defined at the outset display an enhanced solubility in water, compared to the racemic mixture, and almost the same or the same or preferably an enhanced solubility in water, compared to the pure L-isomer, but they are easier with respect to manufacture.

Therefore, inventive mixtures are mixtures of L- and D-enantiomers of methyl glycine diacetic acid (MGDA) or its respective mono-, di or trialkali metal or mono-, di or triammonium salts, said mixture containing predominantly the respective L-isomer with an enantiomeric excess (ee) in the range of from 10 to 75%.

The term ammonium salts as used in the present invention refers to salts with at least one cation that bears a nitrogen atom that is permanently or temporarily quaternized. Examples of cations that bear at least one nitrogen atom that is permanently quaternized include tetramethylammonium, tetraethylammonium, dimethyldiethyl ammonium, and n-$C_{10}$-$C_{20}$-alkyl trimethyl ammonium. Examples of Examples of cations that bear at least one nitrogen atom that is temporarily quaternized include protonated amines and ammonia, such as monomethyl ammonium, dimethyl ammonium, trimethyl ammonium, monoethyl ammonium, diethyl ammonium, triethyl ammonium, n-$C_{10}$-$C_{20}$-alkyl dimethyl ammonium 2-hydroxyethylammonium, bis(2-hydroxyethyl) ammonium, tris(2-hydroxyethyl)ammonium, N-methyl 2-hydroxyethyl ammonium, N,N-dimethyl-2-hydroxyethylammonium, and especially $NH_4^+$.

In one embodiment of the present invention, inventive mixtures are mixtures of L- and D-enantiomers of molecules of general formula (I)

$$[CH_3-CH(COO)-N(CH_2-COO)_2]M_{3-x}H_x \qquad (I)$$

wherein
x is in the range of from zero to 0.5, preferably from zero to 0.25,

M is selected from ammonium, substituted or non-substituted, and potassium and sodium and mixtures thereof, preferably sodium.

Preferred are the trialkali metal salts of MGDA such as the tripotassium salts and even more preferred are the trisodium salts.

In one embodiment of the present invention, the enantiomeric excess of the respective L-isomer in inventive mixtures is in the range of from 10 to 75%, preferably in the range of from 12.5 to 60%.

In embodiments where two or more compounds are present, the ee refers to the enantiomeric excess of all L-isomers present in the mixture compared to all D-isomers. For example, in cases wherein a mixture of the di- and trisodium salt of MGDA is present, the ee refers to the sum of the disodium salt and trisodium salt of L-MGDA with respect to the sum of the disodium salt and the trisodium salt of D-MGDA.

The enantiomeric excess can be determined by measuring the polarization (polarimetry) or preferably by chromatography, for example by HPLC with a chiral column, for example with one or more cyclodextrins as immobilized phase or with a ligand exchange (Pirkle-brush) concept chiral stationary phase. Preferred is determination of the ee by HPLC with an immobilized optically active amine such as D-penicillamine in the presence of copper(II) salt.

In one embodiment of the present invention, inventive mixtures may contain in the range of from 0.1 to 10% by weight of one or more optically inactive impurities, at least one of the impurities being at least one of the impurities being selected from iminodiacetic acid, formic acid, glycolic acid, propionic acid, acetic acid and their respective alkali metal or mono-, di- or triammonium salts.

In one aspect of the present invention, inventive mixtures may contain less than 0.2% by weight of nitrilotriacetic acid (NTA), preferably 0.01 to 0.1% by weight.

In one aspect of the present invention, inventive mixtures may contain minor amounts of cations other than alkali metal or ammonium. It is thus possible that minor amounts, such as 0.01 to 5 mol-% of total chelating agent inventive mixture, based on anion, bear alkali earth metal cations such as $Mg^{2+}$ or $Ca^{2+}$, or transition metal ions such as $Fe^{2+}$ or $Fe^{3+}$ cations.

Inventive mixtures display a very good solubility, especially in water and aqueous alkali metal hydroxide solutions. Such very good solubility can be seen, e.g., in a temperature range of from zero ° C. to 40° C., in particular at room temperature and/or at zero and/or +10° C.

Another aspect of the present invention is therefore an aqueous solution of an inventive mixture, containing in the range of from 40 to 60% by weight of said inventive mixture, preferably 45 to 58% by weight, even more preferably 48 to 55% by weight. Such aqueous solutions are hereinafter also being referred to as inventive solutions or solutions according to the present invention. Inventive solutions do not show amounts of precipitation or crystallization on addition of seed crystals or mechanical stress. Inventive solutions do not exhibit any visible turbidity.

In a preferred embodiment of the present invention, solutions according to the present invention are free from surfactants. Free from surfactants shall mean, in the context of the present invention, that the total contents of surfactants is 0.1% by weight or less, referring to the amount of inventive mixture. In a preferred embodiment, the term "free from surfactants" shall encompass a concentration in the range of from 50 ppm to 0.05%, both ppm and % referring to ppm by weight or % by weight, respectively, and referring to the total respective inventive solution.

In a preferred embodiment of the present invention, solutions according to the present invention are free from organic polymers. Free from organic polymers shall mean, in the context of the present invention, that the total contents of organic polymers is 0.1% by weight or less, referring to the amount of inventive mixture. In a preferred embodiment, the term "free from organic polymers" shall encompass a concentration in the range of from 50 ppm to 0.05%, both ppm and % referring to ppm by weight or % by weight, respectively, and referring to the total respective inventive solution. Organic polymers shall also include organic copolymers and shall include polyacrylates, polyethylene imines, and polyvinylpyrollidone. Organic (co)polymers in the context of the present invention shall have a molecular weight ($M_w$) of 1,000 g or more.

In a preferred embodiment of the present invention, inventive solutions do not contain major amounts of alkali metal of mono- and dicarboxylic acids such as acetic acid, propionic acid, maleic acid, acrylic acid, adipic acid, succinic acid, and the like. Major amounts in this context refer to amounts over 0.5% by weight.

In one embodiment of the present invention, inventive solutions have a pH value in the range of from 8 to 14, preferably 10.0 to 13.5.

In one embodiment of the present invention, inventive solutions additionally contain at least one inorganic basic salt selected from alkali metal hydroxides and alkali metal carbonates. Preferred examples are sodium carbonate, potassium carbonate, potassium hydroxide and in particular sodium hydroxide, for example 0.1 to 1.5% by weight. Potassium hydroxide or sodium hydroxide, respectively, may result from the manufacture of the respective inventive solution.

Furthermore, inventive mixtures as well as inventive solutions may contain one or more inorganic non-basic salts such as—but not limited to—alkali metal halide or preferably alkali metal sulphate, especially potassium sulphate or even more preferably sodium sulphate. The content of inorganic non-basic salt may be in the range of from 0.10 to 1.5% by weight, referring to the respective inventive mixture or the solids content of the respective inventive solution. Even more preferably, inventive mixtures as well as inventive solutions do not contain significant amounts of inorganic non-basic salt, for example in the range of from 50 ppm to 0.05% by weight, referring to the respective inventive mixture or the solids content of the respective inventive solution. Even more preferably inventive mixtures contain 1 to 50 ppm by weight of sum of chloride and sulphate, referring to the respective inventive mixture. The contents of sulphate may be determined, for example, by gravimetry or by ion chromatography.

Furthermore, inventive mixtures as well as inventive solutions exhibit advantageous olfactory behaviour as well as a very low tendency to colorize such as yellowing upon storage.

Furthermore, inventive mixtures as well as inventive solutions display advantageous behaviour towards bleaching agents such as sodium percarbonate, and inventive mixtures are less hygroscopic than the racemic mixture of MGDA. Inventive mixtures form free flowing powders more readily than the racemic mixture of MGDA.

Furthermore, inventive mixtures display an improved behaviour towards strong bases such as solid potassium hydroxide or solid sodium hydroxide. When stored as a mixture with solid potassium hydroxide or solid sodium hydroxide and later formulated in water, they can be formulated as clear, non-turbid solutions with good shelve-life.

Inventive mixtures may be prepared by mixing the respective quantities of enantiomerically pure L-MGDA and D-MGDA or their respective salts. However, the manufacture of enantiomerically pure D-MGDA is tedious, and other processes of making inventive mixtures have been found in the context of the present invention.

A further aspect of the present invention is a process for making inventive mixtures, hereinafter also being referred to as inventive process. The inventive process comprises the steps of
(a) dissolving a mixture of L-alanine and its alkali metal salt in water,
(b) converting said mixture of L-alanine and its alkali metal salt with formaldehyde and hydrocyanic acid or alkali metal cyanide to a dinitrile,
(c) saponification of the dinitrile resulting from step (b) in two steps (c1) and (c2), steps (c1) and (c2) being carried out at different temperatures, employing stoichiometric amounts of hydroxide or an excess of 1.01 to 1.5 moles of hydroxide per molar sum of COOH groups and nitrile groups of dinitrile from step (b).

The inventive process will be described in more detail below.

In step (a) of the inventive process, a mixture of L-alanine and the alkali metal salt of L-alanine is being dissolved in water. L-alanine in the context of the present invention refers to either pure L-alanine with non-detectable amounts of D-alanine, or to mixtures of enantiomers of L-alanine and D-alanine, the enantiomeric excess being at least 96%, preferably at least 98%. The purer the enantiomer L-alanine, the better is the steering of the racemization in step (c) of the inventive process.

Of the alkali metal salts, the potassium salt is preferred and the sodium salt is even more preferred.

There are various ways to perform step (a) of the inventive process. It is possible to prepare a solid mixture of L-alanine and the alkali metal salt of L-alanine and to then dissolve the mixture so obtained in water. It is preferred, though, to slurry L-alanine in water and to then add the required amount alkali metal hydroxide, as solid or as aqueous solution.

In one embodiment of the present invention, step (a) of the inventive process is being carried out at a temperature in the range of from 5 to 70° C., preferably in the range of from 15 to 60° C. During the performance of step (a), in many instances a raise of temperature can be observed, especially when the embodiment of slurrying L-alanine in water and to then add the required amount alkali metal hydroxide, as solid or as aqueous solution, has been chosen.

An aqueous solution of a mixture of L-alanine and its corresponding alkali metal salt will obtained from step (a).

In one embodiment of step (a), an aqueous solution of a mixture of the range of from 10 to 50 mole-% of L-alanine (free acid) and of 50 to 90 mole-% of L-alanine (alkali metal salt) is being obtained. Particularly preferred are mixtures of 23 to 27 mole-% of L-alanine (free acid) and 63 to 67 mole% of the alkali metal salt of L-alanine is being obtained.

Preferably, an aqueous solution of a mixture of L-alanine and its corresponding alkali metal salt may have a total solids content in the range of from 10 to 35%. Preferably, such aqueous solution of a mixture of L-alanine and its corresponding alkali metal salt may have a pH value in the range of from 6 to 12.

Preferably, the aqueous solution obtained from step (a) contains less than 0.5% by weight, impurities other than D-alanine and its corresponding alkali metal salt, the percentage being based on the total solids content of the aqueous solution. Such potential impurities may be one or more of magnesium or calcium salts of inorganic acids. Trace amounts of impurities stemming from the L-alanine or the water used shall be neglected in the further context with the present invention.

In step (b) of the inventive process, a double Strecker synthesis is being carried out by treating the aqueous solution of the mixture of L-alanine and its alkali metal salt obtained in step (a) with formaldehyde and hydrocyanic acid or alkali metal cyanide. The double Strecker synthesis can be carried out by adding alkali metal cyanide or a mixture from hydrocyanic acid and alkali metal alkali metal cyanide) or preferably hydrocyanic acid and formaldehyde to the aqueous solution obtained in step (a). Said addition of formaldehyde and alkali metal cyanide or preferably hydrocyanic acid can be performed in one or more portions. Formaldehyde can be added as gas or as formalin solution or as paraformaldehyde. Preferred is the addition of formaldehyde as 30 to 35% by weight aqueous solution.

In a particular embodiment of the present invention, step (b) of the inventive process is being carried out at a temperature in the range of from 20 to 80° C., preferably from 35 to 65° C.

In one embodiment of the present invention, step (b) of the inventive process is being carried out at a constant temperature in the above range. In another embodiment, step (b) of the inventive process is being carried using a temperature profile, for example by starting the reaction at 40° C. and allowing then stirring the reaction mixture at 50° C.

In one embodiment of the present invention, step (b) of the inventive process is being carried out at elevated pressure, for example 1.01 to 6 bar. In another embodiment, step (b) of the inventive process is being carried at normal pressure (1 bar).

In one embodiment of the present invention, step (b) of the inventive process is being carried out at a constant pH value, and a base or an acid is being added in order to keep the pH value constant. Preferably, however, the pH value during step (b) is decreasing, and neither base nor acid other than, optionally, HCN is being added. In such embodiments, at the end of step (b), the pH value may have dropped to 2 to 4.

Step (b) can be performed in any type of reaction vessel that allows the handling of hydrocyanic acid. Useful are, for example, flasks, stirred tank reactors and cascades of two or more stirred tank reactors.

From step (b), an aqueous solution of the L-enantiomer, a dinitrile of formula (B)

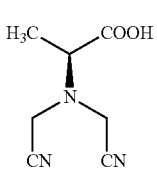

(B)

and its corresponding alkali metal salt will be obtained, briefly also referred to as dinitrile (B) or alkali metal salt of dinitrile (B), respectively.

In step (c), the dinitrile resulting from step (b) will be saponified in two steps (c1) and (c2) at different temperatures, employing stoichiometric amounts of hydroxide or an excess of 1.01 to 1.5 moles of hydroxide per molar sum of COOH groups and nitrile groups of dinitrile of step (b), preferably 1.01 to 1.2 moles.

Different temperature means in the context of step (c) that the average temperature of step (c1) is different from the average temperature of step (c2). Preferably, step (c1) is being performed at a temperature lower than step (c2). Even more preferably, step (c2) is being performed at an average temperature that is at least 100° C. higher than the average temperature of step (c1). Hydroxide in the context of step (c) refers to alkali metal hydroxide, preferably potassium hydroxide and even more preferably to sodium hydroxide.

Step (c1) can be started by adding the solution resulting from step (b) to an aqueous solution of alkali metal hydroxide or adding an aqueous solution of alkali metal hydroxide to a solution resulting from step (b). In another embodiment, the solution resulting from step (b) and an aqueous solution of alkali metal hydroxide are being added simultaneously to a vessel.

When calculating the stoichiometric amounts of hydroxide to be added in step (c1), the sum of COOH groups and nitrile groups from the total theoretical amount of dinitrile (B) is multiplied by 3 and the amounts of alkali already present from step (a) and, optionally, step (b), is subtracted.

Step (c1) can be performed at a temperature in the range of from 20 to 80° C., preferable 40 to 70° C. In the context of step (c1) "temperature" refers to the average temperature.

As a result of step (c1), an aqueous solution of the respective diamide and its respective alkali metal salt can be obtained, M being alkali metal. Said solution may also contain L-MGDA and the corresponding monoamide and/or its mono- or dialkali metal salt.

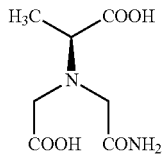

Step (c2) can be performed at a temperature in the range of from 130 to 195° C., preferably 175 to 195° C. In the context of step (c1) "temperature" refers to the average temperature.

In one embodiment of the present invention, step (c2) has an average residence time in the range of from 5 to 180 minutes.

In preferred embodiments the higher range of the temperature interval of step (c2) such as 190 to 195° C. is combined with a short residence time such as 20 to 25 minutes, or the lower range of the temperature interval of step (c2) such as 175° C. to 180° C. is combined with a longer residence time such as 50 to 60 minutes, or a middle temperature such as 185° C. is combined with a middle residence time such as 35 to 45 minutes.

Step (c2) can be performed in the same reactor as step (c1), or—in the case of a continuous process—in a different reactor.

In one embodiment of the present invention step (c2) is carried out with an excess of base of 1.01 to 1.2 moles of hydroxide per mole of nitrile group.

Depending on the type of reactor in which step (c2) is being performed, such as an ideal plug flow reactor, the average residence time can be replaced by the residence time.

In one embodiment of the present invention, step (c1) is being carried out in a continuous stirred tank reactor and step (c2) is being carried out in a second continuous stirred tank reactor. In a preferred embodiment, step (c1) is being carried out in a continuous stirred tank reactor and step (c2) is being carried out in a plug flow reactor, such as a tubular reactor.

In one embodiment of the present invention, step (c1) of the inventive process is being carried out at elevated pressure, for example at 1.05 to 6 bar. In another embodiment, step (c1) of the inventive process is being carried at normal pressure.

Especially in embodiments wherein step (c2) is being carried out in a plug flow reactor, step (c2) may be carried out at elevated pressure such as 1.5 to 40 bar, preferably at least 20 bar. The elevated pressure may be accomplished with the help of a pump or by autogenic pressure elevation.

Preferably, the pressure conditions of steps (c1) and (c2) are combined in the way that step (c2) is carried out at a higher pressure than step (c1).

During step (c2), a partial racemization takes place. Without wishing to be bound by any theory, it is likely that racemization takes place on the stage of of the above L-diamide or of L-MGDA.

In one embodiment of the present invention, the inventive process may comprise steps other than steps (a), (b) and (c) disclosed above. Such additional steps may be, for example, one or more decolourization steps, for example with activated carbon or with peroxide such as $H_2O_2$.

A further step other than step (a), (b) or (c) that is preferably carried out after step (c2) is stripping with nitrogen or steam in order to remove ammonia. Said stripping can be carried out at temperatures in the range of from 90 to 110° C. By nitrogen or air stripping, water can be removed from the solution so obtained. Stripping is preferably carried out at a pressure below normal pressure, such as 650 to 950 mbar.

In embodiments wherein an inventive solution is desired, the solution obtained from step (c2) is just cooled down and, optionally, concentrated by partially removing the water. If dry samples of inventive mixtures are required, the water can be removed by spray drying or spray granulation.

The inventive process may be carried out as a batch process, or as a semi-continuous or continuous process.

A further aspect of the present invention is the use of an inventive mixture or an inventive solution for the manufacture of laundry detergent compositions and of detergent compositions for cleaners. A further aspect is a process for manufacture of laundry detergents and of detergent compositions cleaners by using an inventive mixture or an inventive solution. Depending on whether a mixing in aqueous formulation or in dry matter is desired, and depending on whether a liquid or solid detergent composition is desired, an inventive aqueous solution or an inventive mixture of isomers can be used. Mixing can be performed by formulation steps known per se.

In particular when mixing is being carried out with an inventive solution for the production of a solid laundry detergent compositions or a solid detergent composition for cleaners, such use is advantageous because it allows to add only reduced amounts of water to be removed later, and it allows for great flexibility because no additional ingredients such as polymer, surfactants or salts are present that otherwise reduce flexibility of the detergent manufacturer.

In one embodiment of the present invention, inventive aqueous solutions may be used as such for the manufacture of laundry detergent compositions or for detergent compositions for cleaners. In other embodiments, inventive aqueous solutions may be used in fully or preferably partially neutralized form for the manufacture of laundry detergent compositions or for detergent compositions for cleaners. In one embodiment, inventive aqueous solutions may be used in fully or preferably partially neutralized form for the manufacture of laundry detergent compositions or of detergent compositions for cleaners, said neutralization being performed with an inorganic acid (mineral acid). Preferred inorganic acids are selected from $H_2SO_4$, HCl, and $H_3PO_4$. In other embodiments, inventive aqueous solutions may be used in fully or preferably partially neutralized form for the manufacture of laundry detergent compositions or of detergent compositions for cleaners, said neutralization being performed with an organic acid. Preferred organic acids are selected from $CH_3SO_3H$, acetic acid, propionic acid, and citric acid.

In the context of the present invention, the term "detergent composition for cleaners" includes cleaners for home care and for industrial or institutional applications. The term "detergent composition for cleaners" includes compositions for dishwashing, especially hand dishwash and automatic dishwashing and ware-washing, and compositions for hard surface cleaning such as, but not limited to compositions for bathroom cleaning, kitchen cleaning, floor cleaning, descaling of pipes, window cleaning, car cleaning including truck cleaning, furthermore, open plant cleaning, cleaning-in-place, metal cleaning, disinfectant cleaning, farm cleaning, high pressure cleaning, but not laundry detergent compositions.

In the context of the present invention and unless expressly stated otherwise, percentages in the context of ingredients of laundry detergent compositions are percentages by weight and refer to the total solids content of the respective laundry detergent composition. In the context of the present invention and unless expressly stated otherwise, percentages in the context of ingredients of detergent composition for cleaners are percentages by weight and refer to the total solids content of the detergent composition for cleaner.

In one embodiment of the present invention, laundry detergent compositions according to the present invention may contain in the range of from 1 to 30% by weight of inventive mixture. Percentages refer to the total solids content of the respective laundry detergent composition.

In one embodiment of the present invention, detergent compositions for cleaners according to the present invention may contain in the range of from 1 to 50% by weight of inventive mixture, preferably 5 to 40% by weight and even more preferably 10 to 25% by weight. Percentages refer to the total solids content of the respective detergent composition for home care.

Particularly advantageous laundry detergent compositions and of detergent compositions for cleaners, especially for home care may contain one or more complexing agent other than MGDA. Advantageous detergent compositions for cleaners and advantageous laundry detergent compositions may contain one or more complexing agent (in the context of the present invention also referred to as sequestrant) other than a mixture according to the present invention. Examples for sequestrants other than a mixture according to the present invention are GLDA, IDS (iminodisuccinate), citrate, phosphonic acid derivatives, for example the disodium salt of hydroxyethane-1,1-diphosphonic acid ("HEDP"), and polymers with complexing groups like, for example, polyethyleneimine in which 20 to 90 mole-% of the N-atoms bear at least one $CH_2COO^-$ group, and their respective alkali metal salts, especially their sodium salts, for example $GLDA-Na_4$, $IDS-Na_4$, and trisodium citrate, and phosphates such as STPP (sodium tripolyphosphate). Due to the fact that phosphates raise environmental concerns, it is preferred that advantageous detergent compositions for cleaners and advantageous laundry detergent compositions are free from phosphate. "Free from phosphate" should be understood in the context of the present invention, as meaning that the content of phosphate and polyphosphate is in sum in the range from 10 ppm to 0.2% by weight, determined by gravimetry.

Advantageous detergent compositions for cleaners and advantageous laundry detergent compositions may contain one or more surfactant, preferably one or more non-ionic surfactant.

Preferred non-ionic surfactants are alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (I)

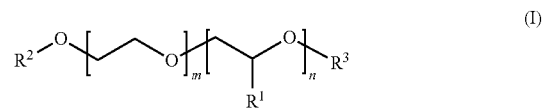

(I)

in which the variables are defined as follows:
$R^1$ is identical or different and selected from hydrogen and linear $C_1$-$C_{10}$-alkyl, preferably in each case identical and ethyl and particularly preferably hydrogen or methyl,
$R^2$ is selected from $C_8$-$C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$,
$R^3$ is selected from $C_1$-$C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or isodecyl,
m and n are in the range from zero to 300, where the sum of n and m is at least one, preferably in the range of from 3 to 50. Preferably, m is in the range from 1 to 100 and n is in the range from 0 to 30.

In one embodiment, compounds of the general formula (I) may be block copolymers or random copolymers, preference being given to block copolymers.

Other preferred examples of alkoxylated alcohols are, for example, compounds of the general formula (II)

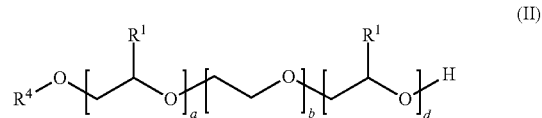

(II)

in which the variables are defined as follows:
$R^1$ is identical or different and selected from hydrogen and linear $C_1$-$C_0$-alkyl, preferably identical in each case and ethyl and particularly preferably hydrogen or methyl,
$R^4$ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$, a is a number in the range from zero to 10, preferably from 1 to 6, b is a number in the range from 1 to 80, preferably from 4 to 20, d is a number in the range from zero to 50, preferably 4 to 25.

The sum a+b+d is preferably in the range of from 5 to 100, even more preferably in the range of from 9 to 50.

Preferred examples for hydroxyalkyl mixed ethers are compounds of the general formula (III)

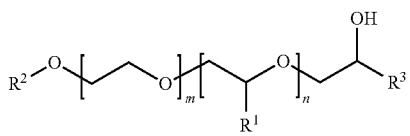

(III)

in which the variables are defined as follows:

$R^1$ is identical or different and selected from hydrogen and linear $C_1$-$C_{10}$-alkyl, preferably in each case identical and ethyl and particularly preferably hydrogen or methyl, $R^2$ is selected from $C_8$-$C_{22}$-alkyl, branched or linear, for example iso-$C_{11}H_{23}$, iso-$C_{13}H_{27}$, n-$C_8H_{17}$, n-$C_{10}H_{21}$, n-$C_{12}H_{25}$, n-$C_{14}H_{29}$, n-$C_{16}H_{33}$ or n-$C_{18}H_{37}$, $R^3$ is selected from $C_1$-$C_{18}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The integers m and n are in the range from zero to 300, where the sum of n and m is at least one, preferably in the range of from 5 to 50. Preferably, m is in the range from 1 to 100 and n is in the range from 0 to 30.

Compounds of the general formula (II) and (III) may be block copolymers or random copolymers, preference being given to block copolymers.

Further suitable nonionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{16}$-alkyl polyglucosides and branched $C_8$-$C_{14}$-alkyl polyglycosides such as compounds of general average formula (IV) are likewise suitable.

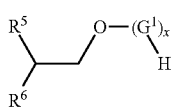

(IV)

wherein the integers are defined as follows:

$R^5$ is $C_1$-$C_4$-alkyl, in particular ethyl, n-propyl or isopropyl, $R^6$ is —$(CH_2)_2$—$R^5$, $G^1$ is selected from monosaccharides with 4 to 6 carbon atoms, especially from glucose and xylose, x in the range of from 1.1 to 4, x being an average number, y is a number in the range of from zero to 3.

Further examples of non-ionic surfactants are compounds of general formula (V) and (VI)

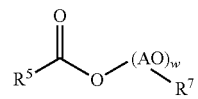

(V)

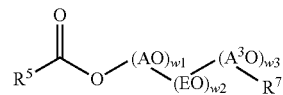

(VI)

AO is selected from ethylene oxide, propylene oxide and butylene oxide,

EO is ethylene oxide, $CH_2CH_2$—O, $R^7$ selected from $C_8$-$C_{18}$-alkyl, branched or linear $A^3O$ is selected from propylene oxide and butylene oxide, w is a number in the range of from 15 to 70, preferably 30 to 50, w1 and w3 are numbers in the range of from 1 to 5, and w2 is a number in the range of from 13 to 35.

An overview of suitable further nonionic surfactants can be found in EP-A 0 851 023 and in DE-A 198 19 187.

Mixtures of two or more different nonionic surfactants may also be present.

Other surfactants that may be present are selected from amphoteric (zwitterionic) surfactants and anionic surfactants and mixtures thereof.

Examples of amphoteric surfactants are those that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteris surfactants is cocamidopropyl betaine (lauramidopropyl betaine).

Examples of amine oxide surfactants are compounds of the general formula (VII)

$R^8R^9R^{10}N{\rightarrow}O$ (VII)

wherein $R^{10}$, $R^8$ and $R^9$ are selected independently from each other from aliphatic, cycloaliphatic or $C_2$-$C_4$-alkylene $C_{10}$-$C_{20}$-alkylamido moieties. Preferably, $R^{10}$ is selected from $C_8$-$C_{20}$-alkyl or $C_2$-$C_4$-alkylene $C_{10}$-$C_{20}$-alkylamido and $R^8$ and $R^9$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

Examples of suitable anionic surfactants are alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Further examples for suitable anionic surfactants are soaps, for example the sodium or potassium salts of stearoic acid, oleic acid, palmitic acid, ether carboxylates, and alkylether phosphates.

Preferably, laundry detergent compositions contain at least one anionic surfactant.

In one embodiment of the present invention, laundry detergent compositions may contain 0.1 to 60% by weight of at least one surfactant, selected from anionic surfactants, amphoteric surfactants and amine oxide surfactants.

In one embodiment of the present invention, detergent compositions for cleaners may contain 0.1 to 60% by weight of at least one surfactant, selected from anionic surfactants, amphoteric surfactants and amine oxide surfactants.

In a preferred embodiment, detergent compositions for cleaners and especially those for automatic dishwashing do not contain any anionic surfactant.

Detergent compositions for cleaners and laundry detergent compositions may contain at least one bleaching agent, also referred to as bleach. Bleaching agents may be selected from chlorine bleach and peroxide bleach, and peroxide bleach may be selected from inorganic peroxide bleach and organic peroxide bleach. Preferred are inorganic peroxide bleaches, selected from alkali metal percarbonate, alkali metal perborate and alkali metal persulfate.

Examples of organic peroxide bleaches are organic percarboxylic acids, especially organic percarboxylic acids.

Suitable chlorine-containing bleaches are, for example, 1,3-dichloro-5,5-dimethylhydantoin, N-chlorosulfamide, chloramine T, chloramine B, sodium hypochlorite, calcium hypochlorite, magnesium hypochlorite, potassium hypochlorite, potassium dichloroisocyanurate and sodium dichloroisocyanurate.

Detergent compositions for cleaners and laundry detergent compositions may comprise, for example, in the range from 3 to 10% by weight of chlorine-containing bleach.

Detergent compositions for cleaners and laundry detergent compositions may comprise one or more bleach catalysts. Bleach catalysts can be selected from bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and also cobalt-, iron-, copper- and ruthenium-amine complexes can also be used as bleach catalysts.

Detergent compositions for cleaners and laundry detergent compositions may comprise one or more bleach activators, for example N-methylmorpholinium-acetonitrile salts ("MMA salts"), trimethylammonium acetonitrile salts, N-acylimides such as, for example, N-nonanoylsuccinimide, 1,5-diacetyl-2,2-dioxohexahydro-1,3,5-triazine ("DADHT") or nitrile quats (trimethylammonium acetonitrile salts).

Further examples of suitable bleach activators are tetraacetylethylenediamine (TAED) and tetraacetylhexylenediamine.

Detergent compositions for cleaners and laundry detergent compositions may comprise one or more corrosion inhibitors. In the present case, this is to be understood as including those compounds which inhibit the corrosion of metal. Examples of suitable corrosion inhibitors are triazoles, in particular benzotriazoles, bisbenzotriazoles, aminotriazoles, alkylaminotriazoles, also phenol derivatives such as, for example, hydroquinone, pyrocatechol, hydroxyhydroquinone, gallic acid, phloroglucinol or pyrogallol.

In one embodiment of the present invention, detergent compositions for cleaners and laundry detergent compositions comprise in total in the range from 0.1 to 1.5% by weight of corrosion inhibitor.

Detergent compositions for cleaners and laundry detergent compositions may comprise one or more builders, selected from organic and inorganic builders. Examples of suitable inorganic builders are sodium sulfate or sodium carbonate or silicates, in particular sodium disilicate and sodium metasilicate, zeolites, sheet silicates, in particular those of the formula $\alpha$-$Na_2Si_2O_5$, $\beta$-$Na_2Si_2O_5$, and $\delta$-$Na_2Si_2O_5$, also fatty acid sulfonates, $\alpha$-hydroxypropionic acid, alkali metal malonates, fatty acid sulfonates, alkyl and alkenyl disuccinates, tartaric acid diacetate, tartaric acid monoacetate, oxidized starch, and polymeric builders, for example polycarboxylates and polyaspartic acid.

Examples of organic builders are especially polymers and copolymers. In one embodiment of the present invention, organic builders are selected from polycarboxylates, for example alkali metal salts of (meth)acrylic acid homopolymers or (meth)acrylic acid copolymers.

Suitable comonomers are monoethylenically unsaturated dicarboxylic acids such as maleic acid, fumaric acid, maleic anhydride, itaconic acid and citraconic acid. A suitable polymer is in particular polyacrylic acid, which preferably has an average molecular weight $M_w$ in the range from 2000 to 40 000 g/mol, preferably 2000 to 10 000 g/mol, in particular 3000 to 8000 g/mol. Also of suitability are copolymeric polycarboxylates, in particular those of acrylic acid with methacrylic acid and of acrylic acid or methacrylic acid with maleic acid and/or fumaric acid, and in the same range of molecular weight.

It is also possible to use copolymers of at least one monomer from the group consisting of monoethylenically unsaturated $C_3$-$C_{10}$-mono- or $C_4$-$C_{10}$-dicarboxylic acids or anhydrides thereof, such as maleic acid, maleic anhydride, acrylic acid, methacrylic acid, fumaric acid, itaconic acid and citraconic acid, with at least one hydrophilic or hydrophobic monomer as listed below.

Suitable hydrophobic monomers are, for example, isobutene, diisobutene, butene, pentene, hexene and styrene, olefins with 10 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene, $C_{22}$-$\alpha$-olefin, a mixture of $C_{20}$-$C_{24}$-$\alpha$-olefins and polyisobutene having on average 12 to 100 carbon atoms per molecule.

Suitable hydrophilic monomers are monomers with sulfonate or phosphonate groups, and also nonionic monomers with hydroxyl function or alkylene oxide groups. By way of example, mention may be made of: allyl alcohol, isoprenol, methoxypolyethylene glycol (meth)acrylate, methoxypolypropylene glycol (meth)acrylate, methoxypolybutylene glycol (meth)acrylate, methoxypoly(propylene oxide-co-ethylene oxide) (meth)acrylate, ethoxypolyethylene glycol (meth)acrylate, ethoxypolypropylene glycol (meth)acrylate, ethoxypolybutylene glycol (meth)acrylate and ethoxypoly (propylene oxide-co-ethylene oxide) (meth)acrylate. Polyalkylene glycols here may comprise 3 to 50, in particular 5 to 40 and especially 10 to 30 alkylene oxide units per molecule.

Particularly preferred sulfonic-acid-group-containing monomers here are 1-acrylamido-1-propanesulfonic acid, 2-acrylamido-2-propanesulfonic acid, 2-acrylamido-2-methylpropanesulfonic acid, 2-methacrylamido-2-methylpropanesulfonic acid, 3-methacrylamido-2-hydroxypropanesulfonic acid, allylsulfonic acid, methallylsulfonic acid, allyloxybenzenesulfonic acid, methal lyloxybenzenesulfonic acid, 2-hydroxy-3-(2-propenyloxy)propanesulfonic acid, 2-methyl-2-propene-1-sulfonic acid, styrenesulfonic acid, vinylsulfonic acid, 3-sulfopropyl acrylate, 2-sulfoethyl methacrylate, 3-sulfopropyl methacrylate, sulfomethacrylamide, sulfomethylmethacrylamide, and salts of said acids, such as sodium, potassium or ammonium salts thereof.

Particularly preferred phosphonate-group-containing monomers are vinylphosphonic acid and its salts.

A further example of builders is carboxymethyl inulin.

Moreover, amphoteric polymers can also be used as builders.

Detergent compositions for cleaners and laundry detergent compositions according to the invention may comprise, for example, in the range from in total 10 to 70% by weight, preferably up to 50% by weight, of builder. In the context of the present invention, MGDA is not counted as builder.

In one embodiment of the present invention, detergent compositions for cleaners and laundry detergent compositions according to the invention may comprise one or more cobuilders.

Detergent compositions for cleaners and laundry detergent compositions may comprise one or more antifoams, selected for example from silicone oils and paraffin oils.

In one embodiment of the present invention, detergent compositions for cleaners and laundry detergent compositions comprise in total in the range from 0.05 to 0.5% by weight of antifoam.

Detergent compositions for cleaners and laundry detergent according to the invention may comprise one or more enzymes. Examples of enzymes are lipases, hydrolases, amylases, proteases, cellulases, esterases, pectinases, lactases and peroxidases.

In one embodiment of the present invention, detergent compositions for cleaners and laundry detergent compositions according to the present invention may comprise, for example, up to 5% by weight of enzyme, preference being given to 0.1 to 3% by weight. Said enzyme may be stabilized, for example with the sodium salt of at least one $C_1$-$C_3$-carboxylic acid or $C_4$-$C_{10}$-dicarboxylic acid. Preferred are formates, acetates, adipates, and succinates.

In one embodiment of the present invention, detergent compositions for cleaners and laundry detergent compositions according to the invention comprise at least one zinc salt. Zinc salts can be selected from water-soluble and water-insoluble zinc salts. In this connection, within the context of the present invention, water-insoluble is used to refer to those zinc salts which, in distilled water at 25° C., have a solubility of 0.1 g/l or less. Zinc salts which have a higher solubility in water are accordingly referred to within the context of the present invention as water-soluble zinc salts.

In one embodiment of the present invention, zinc salt is selected from zinc benzoate, zinc gluconate, zinc lactate, zinc formate, $ZnCl_2$, $ZnSO_4$, zinc acetate, zinc citrate, $Zn(NO_3)_2$, $Zn(CH_3SO_3)_2$ and zinc gallate, preferably $ZnCl_2$, $ZnSO_4$, zinc acetate, zinc citrate, $Zn(NO_3)_2$, $Zn(CH_3SO_3)_2$ and zinc gallate.

In another embodiment of the present invention, zinc salt is selected from ZnO, ZnO.aq, $Zn(OH)_2$ and $ZnCO_3$. Preference is given to ZnO.aq.

In one embodiment of the present invention, zinc salt is selected from zinc oxides with an average particle diameter (weight-average) in the range from 10 nm to 100 μm.

The cation in zinc salt can be present in complexed form, for example complexed with ammonia ligands or water ligands, and in particular be present in hydrated form. To simplify the notation, within the context of the present invention, ligands are generally omitted if they are water ligands.

Depending on how the pH of mixture according to the invention is adjusted, zinc salt can change. Thus, it is for example possible to use zinc acetate or $ZnCl_2$ for preparing formulation according to the invention, but this converts at a pH of 8 or 9 in an aqueous environment to ZnO, $Zn(OH)_2$ or ZnO.aq, which can be present in non-complexed or in complexed form.

Zinc salt may be present in those detergent compositions for cleaners according to the invention which are solid at room temperature are preferably present in the form of particles which have for example an average diameter (number-average) in the range from 10 nm to 100 μm, preferably 100 nm to 5 μm, determined for example by X-ray scattering.

Zinc salt may be present in those detergent compositions for home which are liquid at room temperature in dissolved or in solid or in colloidal form.

In one embodiment of the present invention, detergent compositions for cleaners and laundry detergent compositions comprise in total in the range from 0.05 to 0.4% by weight of zinc salt, based in each case on the solids content of the composition in question.

Here, the fraction of zinc salt is given as zinc or zinc ions. From this, it is possible to calculate the counterion fraction.

In one embodiment of the present invention, detergent compositions for cleaners and laundry detergent compositions according to the invention are free from heavy metals apart from zinc compounds. Within the context of the present, this may be understood as meaning that detergent compositions for cleaners and laundry detergent compositions according to the invention are free from those heavy metal compounds which do not act as bleach catalysts, in particular of compounds of iron and of bismuth. Within the context of the present invention, "free from" in connection with heavy metal compounds is to be understood as meaning that the content of heavy metal compounds which do not act as bleach catalysts is in sum in the range from 0 to 100 ppm, determined by the leach method and based on the solids content. Preferably, formulation according to the invention has, apart from zinc, a heavy metal content below 0.05 ppm, based on the solids content of the formulation in question. The fraction of zinc is thus not included.

Within the context of the present invention, "heavy metals" are deemed to be all metals with a specific density of at least 6 g/cm³ with the exception of zinc. In particular, the heavy metals are metals such as bismuth, iron, copper, lead, tin, nickel, cadmium and chromium.

Preferably, detergent compositions for cleaners and laundry detergent compositions according to the invention comprise no measurable fractions of bismuth compounds, i.e. for example less than 1 ppm.

In one embodiment of the present invention, detergent compositions according to the present invention comprise one or more further ingredient such as fragrances, dyestuffs, organic solvents, buffers, disintegrants for tabs, and/or acids such as methylsulfonic acid.

Preferred example detergent compositions for automatic dishwashing may be selected according to table 1.

TABLE 1

Example detergent compositions for automatic dishwashing

| All amounts in g/sample | ADW.1 | ADW.2 | ADW.3 |
|---|---|---|---|
| inventive mixture, ee: 30.6% | 30 | 22.5 | 15 |
| Protease | 2.5 | 2.5 | 2.5 |
| Amylase | 1 | 1 | 1 |
| n-$C_{18}H_{37}$—O($CH_2CH_2O)_9H$ | 5 | 5 | 5 |
| Polyacrylic acid $M_w$ 4000 g/mol as sodium salt, completely neutralized | 10 | 10 | 10 |
| Sodium percarbonate | 10.5 | 10.5 | 10.5 |

TABLE 1-continued

Example detergent compositions for automatic dishwashing

| All amounts in g/sample | ADW.1 | ADW.2 | ADW.3 |
|---|---|---|---|
| TAED | 4 | 4 | 4 |
| $Na_2Si_2O_5$ | 2 | 2 | 2 |
| $Na_2CO_3$ | 19.5 | 19.5 | 19.5 |
| Sodium citrate dihydrate | 15 | 22.5 | 30 |
| HEDP | 0.5 | 0.5 | 0.5 |
| ethoxylated polyethylenimine, 20 EO/NH group, $M_n$: 30,000 g/mol | optionally: 0.1 | optionally: 0.1 | optionally: 0.1 |

Laundry detergent compositions according to the invention are useful for laundering any type of laundry, and any type of fibres. Fibres can be of natural or synthetic origin, or they can be mixtures of natural of natural and synthetic fibres. Examples of fibers of natural origin are cotton and wool. Examples for fibers of synthetic origin are polyurethane fibers such as Spandex® or Lycra®, polyester fibers, or polyamide fibers. Fibers may be single fibers or parts of textiles such as knitwear, wovens, or nonwovens.

The Invention is Further Illustrated by Working Examples.

General Remarks:

The ee value was determined by HPLC using a Chirex 3126 column; (D)-penicillamine, 5 μm, 250×4.6 mm. The mobile phase (eluent) was 0.5 mM aqueous CuSat-solution. Injection: 10 μl, flow: 1.5 ml/min. Detection by UV light at 254nm. Temperature: 20° C. Running time was 25 min. The ee value was determined as difference of the area % of the L- and D-MGDA peak divided by the sum of area % of L- and D-MGDA peak. Sample preparation: A 10 ml measuring flask was charged with 5 mg of test material and then filled mark with the eluent and then homogenized.

In each case, the solubility was calculated to refer to pure MGDA, without hydrate water.

I. Syntheses of Inventive Mixtures

With exception of ee values, percentages in the context of the examples refer to percent by weight unless expressly indicated otherwise.

I.1 Synthesis of a Solution of Partially Neutralized of L-alanine, Step (a.1)

A 5-liter stirred flask was charged with 2,100 g of de-ionized water and heated to 40° C. 1,200 g of L-alanine (13.47 mol, 98% ee) were added. To the resultant slurry 700 g of 50% by weight aqueous sodium hydroxide solution (8.75 mol) were added over a period of 30 minutes. During the addition the temperature raised to 60° C. After complete addition of the sodium hydroxide the slurry was stirred at 60° for 30 minutes. A clear solution was obtained.

Samples of aqueous L-MGDA-Na3 were prepared according to WO 2012/150155, page 4, lines 26 ff.

I.2 Syntheses of Aqueous Solutions of L-MGDA-$Na_3$, Steps (b.1) and Saponification A 5-liter stirred flask was charged with 500 ml of water and heated to 40° C. Then, 2,373 g of L-alanine solution according to step (a.1) (8.00 mole), 1627 g of 30% by weight aqueous formaldehyde solution (16.27 mole) and 220 g of hydrogen cyanide (8.15 mol) were added simultaneously within 60 minutes. Then, additional 220 g of hydrogen cyanide (8.15 mol) were added at 40° C. within 60 minutes. Upon completion of the addition the reaction mixture was stirred for additional 60 minutes at 40° C. The resulting solution of dinitrile (B) and 1,600 g of sodium hydroxide (50% aqueous solution, 20 mol) were simultaneously added over 160 minutes into another 5-liter stirred flask at a constant rate. During that addition, the temperature was maintained at 28 to 32° C. by external cooling. Upon completion of the addition, the reaction mixture was refluxed for 6 hours at 90 to 95° C. to complete the saponification and to remove any excess of ammonia. The resultant reaction mixture was treated with activated carbon. The resulting aqueous solution contained 38.00 wt % L-MGDA-$Na_3$ and 0.08 wt % trisodium nitrilotriacetate (NTA-$Na_3$). The enantiomeric excess of L-MGDA-$Na_3$ (94.3%) was determined by the aforementioned HPLC method.

The above aqueous solution of MGDA was taken as starting material to investigate the racemization behavior of L-MGDA-$Na_3$: 6 g of the solution were filled into a pressure tube. This tube was sealed and then tempered for a defined period of time (table 2) at 120° C. or 180° C., respectively. Then the solution was cooled to room temperature and the enantiomeric excess was determined by HPLC.

TABLE 2

Heating of L-MGDA-$Na_3$ (6 g of 38% aqueous solution, excess of 0.15 mol NaOH/mol MGDA) in a sealed pressure tube:

| # | Temperature [° C.] | Period [min] | L-MGDA-$Na_3$ [%] | D-MGDA-$Na_3$ [%] | ee [%] |
|---|---|---|---|---|---|
| C-0 | — | — | 97.1 | 2.9 | 94.3 |
| C-(c2.1) | 120 | 60 | 94.4 | 5.6 | 88.8 |
| (c2.2) | 180 | 20 | 78.3 | 21.7 | 56.6 |
| (c2.3) | 180 | 40 | 61.3 | 38.7 | 22.6 |
| (c2.4) | 180 | 60 | 55.8 | 44.2 | 11.6 |

C-0 and C-(c2.1) are comparison experiments.

The inventive mixtures so obtained typically have an NTA-Na3 content of 0.05% by weight with respect to the total solution. Unlike the mixture obtained from C-(c2.1), inventive mixtures displayed an excellent olfactory behavior, and they had a low tendency of yellowing.

I.2 Synthesis of Aqueous Solutions of Inventive Mixtures, Steps (b.1) and (c1.1) and (c2.5) to (c2.7), Continuous Process The continuous syntheses of ca. 40% solutions of inventive mixtures were carried out in cascade of 6 stirred tank reactors, total volume of 8.5 l. The reaction mixture passed all 6 stirred tank reactors (STR.1 to STR.6) consecutively. The last stirred tank reactor to be passed, STR.6, was connected to a tubular reactor, TR.7. In the first three stirred tank reactors, STR.1 to STR.3, dinitrile (B) was synthesized, and STR.1 to STR.3 were operated at 40° C. The average residence time in STR.1 to STR.3 was 45 to 90 min in total. In the three stirred tank reactors STR.4 to STR.6 the saponification was carried out. STR.4 to STR.6 were operated at 60° C. The average residence time in STR.4 to STR.6 was 170 to 400 min in total. The saponification was then completed in tubular reactor TR.7 which was operated with a temperature profile of 130 to 195° C. The final ammonia stripping is done in a column under normal pressure using steam.

Formaldehyde (30% aqueous solution), an aqueous solution of L-alanine (I) and its sodium salt obtained according to 1.1 and 80 mol-% of the required HCN were added to STR.1, the remaining 20% of the required HCN were added to STR.2, the required sodium hydroxide solution was added in STR.4.

The molar ratios of the feed materials were as follows:
Sum of L-alanine and its sodium salt: 1.00,
Formaldehyde=1.95 to 2.05,
HCN=1.95 to 2.10 and
Sodium hydroxide=3.15 (total amount of sodium hydroxide, including sodium hydroxide added in step (a.1).

The 40% by weight solutions of inventive mixtures so obtained typically had an NTA-Na3 content of 0.05-0.10% with respect to the total respective solution. They displayed excellent olfactory behavior, and they had a low tendency of yellowing.

TABLE 3

Influence of temperature and residence time of step (c2.5) to (c2.7)

|  | Temperature [° C.] | Residence time for step (c2) [min] | ee [%] |
|---|---|---|---|
| (c2.5) | 180 | 70 | 10.0 |
| (c2.6) | 180 | 30 | 30.6 |
| (c2.7) | 178 | 30 | 36.2 |

II. Determination of Solubility

The solubility of inventive mixtures and of comparison experiments was determined with an apparatus that allowed heating and cooling down liquid solutions. The temperature (or concentration) of beginning solubility was determined by first cooling down a 50% by weight solution of the respective inventive mixture (or of pure L-MGDA, or of racemic MGDA) to beginning precipitation of MGDA, cooling rate: 30° C./h. Then, the slurry of crystals of MGDA so obtained was again heated at a speed of 1° C./h until a clear solution was obtained. The slurry/solution was checked for solid particles by visible light scattering detection.

The above tests furnished the minimum temperature, $T_{sol}$, for forming a kinetically stable 50% by weight solution of the respective mixture of isomers. A higher temperature $T_{sol}$ correlates with a lower solubility at ambient temperature.

TABLE 4 correlation ee value versus $T_{sol}$

| ee value (%) | $T_{sol}$ [° C.] |
|---|---|
| zero | 103.8 |
| 10.1 | 74.5 |
| 20.0 | 74.0 |
| 50.0 | 68.1 |
| 70.0 | 59.5 |
| 97.7 | 37.0 |

III. Determination of Stability Against Strong alkali

The following tolerance tests were performed: 25 g of a 40% by weight aqueous solution of the respective inventive mixture (or of racemic MGDA) were mixed under one hour of stirring with the amount of solid NaOH beads according to table 5. The mixture so obtained was stored at ambient temperature over the period of up to 96 hours. Then, the appearance was characterized by visual inspection. The results are summarized in table 5.

TABLE 5

Appearance of test solutions after 96 h of storage

| NaOH added [g] | Racemic MGDA | MGDA: 50% ee |
|---|---|---|
| 0 | clear liquid | clear liquid |
| 0.5 | clear liquid | clear liquid |
| 1.0 | clear liquid | clear liquid |
| 1.5 | turbid* liquid | clear liquid |
| 2.0 | turbid* liquid | clear liquid |
| 2.5 | turbid, precipitate** | clear liquid |

*after 48 hours
**immediately after addition of NaOH

The ivention claimed is:

1. A mixture of L- and D-enantiomers of methyl glycine diacetic acid (MGDA) or its respective mono-, di or trialkali metal or mono-, di- or triammonium salts, the mixture comprising predominantly the respective L-isomer with an enantiomeric excess (ee) in the range of from 10 to 75%.

2. The mixture according to claim 1, the enantiomers being selected from the trisodium salts of MGDA.

3. The mixture according to claim 1, the mixture being predominantly the L-isomer with an enantiomeric excess (ee) in the range of from 12.5 to 60%.

4. The mixture according to claim 1, comprising of from 0.1 to 10% by weight of one or more optically inactive impurities, at least one of the impurities being selected from the group consisting of iminodiacetic acid, formic acid, glycolic acid, propionic acid, acetic acid and their respective alkali metal or mono-, di- or triammonium salts.

5. An aqueous solution comprising of from 40 to 60% by weight of a mixture according to claim 1.

6. The aqueous solution according to claim 5, wherein the aqueous solution is free from organic polymer.

7. The aqueous solution according to claim 5, wherein the aqueous solution additionally comprises at least one inorganic salt selected from the group consisting of alkali metal hydroxides and alkali metal carbonates.

8. A process for making a mixture according to claim 1, comprising
(a) dissolving a mixture of L-alanine and its alkali metal salt in water,
(b) converting the mixture of L-alanine and its alkali metal salt with formaldehyde and hydrocyanic acid or alkali metal cyanide to a dinitrile,
(c) performing saponification of the dinitrile resulting from (b) in two steps (c1) and (c2) at different temperatures, employing stoichiometric amounts of hydroxide or an excess of 1.01 to 1.5 moles of hydroxide per molar sum of COOH groups and nitrile groups of the dinitrile from (b).

9. The process according to claim 8, wherein (c1) is carried out at a temperature in the range of from 20 to 80° C. and (c2) is carried out at a temperature in the range of from 175 to 195° C.

10. The process according to claim 8, wherein (c2) has an average residence time in the range of from 20 to 60 minutes.

11. The process according claim 8, wherein (c2) is carried out with an excess of base of 1.01 to 1.2 moles of hydroxide per molar sum of COOH and nitrile groups of the dinitrile from (b).

12. The process according to claim 8, wherein (c2) is carried out at a higher pressure than (c1).

13. The aqueous solution according to claim 5, wherein the aqueous solution is suitable for the manufacture of laundry detergent compositions and of detergent compositions for cleaners.

14. The aqueous solution according to claim 1, wherein the aqueous solution is suitable in fully or partially neutralized form for the manufacture of laundry detergent compositions or of detergent compositions for cleaners, the neutralization being performed with an inorganic acid.

15. The aqueous solution according to claim 1, wherein the aqueous solution is suitable in fully or partially neutralized form for the manufacture of laundry detergent compositions or of detergent compositions for cleaners, the neutralization being performed with an organic acid.

* * * * *